United States Patent [19]

Winter

[11] 4,042,649
[45] Aug. 16, 1977

[54] 1,2-OXAPHOSPHOLANES

[75] Inventor: Roland A. E. Winter, Armonk, N.Y.

[73] Assignee: Ciba-Geigy Corporation, Ardsley, N.Y.

[21] Appl. No.: 614,403

[22] Filed: Sept. 18, 1975

[51] Int. Cl.$^2$ .............................. C07F 9/15; C08K 5/53
[52] U.S. Cl. ............................ 260/927 R; 260/45.7 P; 260/970
[58] Field of Search ......................... 260/927 R, 927 A

[56] References Cited

FOREIGN PATENT DOCUMENTS 819,628   3/1975   Belgium ............................ 260/927 R
2,441,998 3/1975   Germany ........................... 260/927 R

OTHER PUBLICATIONS

Arbuzov et al., "Izv. Akad. Nauk. USSR", Ser. Khim 12, 2757 (1971).

Primary Examiner—Anton H. Sutto
Attorney, Agent, or Firm—Luther A. R. Hall

[57] ABSTRACT

2-Oxo-2-alkoxy-5-dialkylphosphono-1,2-oxaphospholanes of the formula

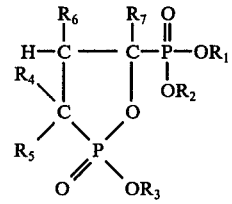

in which $R_1$ to $R_7$ are hydrocarbon radicals can be prepared from $\alpha,\beta$-unsaturated ketones and 2 or more moles of a dialkyl phosphite. Obviously $\gamma$-ketophosphonates are intermediates of this reaction as these compounds react with 1 or more moles of dialkyl phosphite in yielding the oxaphospholanes too. Both reactions are promoted by alkaline catalysts.

The new oxaphospholane derivatives are considerably stable against thermal decomposition. They can be used as flame retardants in epoxy resins.

11 Claims, No Drawings

1,2-OXAPHOSPHOLANES

BACKGROUND OF THE INVENTION

New 1,2-oxaphospholanes are prepared by the reaction of α, β-unsaturated ketones and dialkyl phosphites.

The reaction of dialkyl phosphites with α, β-unsaturated ketones has previously been thoroughly investigated by various experts. It has hitherto been considered the rule that in the reaction only 1 mole of phosphite is added to the double bond forming the γ-ketophosphonates (see Houben-Weyl, Methoden der Organischen Chemie, vol. 12/1, pages 465–467, G. Thieme Verlag, Stuttgart, 1963). If diphosphonates were also obtained, these occured in moderate yield in addition to the monophosphonates (A. N. Pudovik, *Zhurnal Obshch. Khim.* 22, 1371, (1952), *Chem. Abstr.*, 47, 4837, (1953). It was therefore surprising that in the process described herein 2 moles of phosphite are added easily. It was furthermore surprising that the γ-phosphono-α-hydroxyphosphonates evidently formed as intermediate cyclize under the reaction conditions rapidly and virtually completely to give the 1,2-oxaphospholane-5-phosphonates.

The reaction of 1 mole of acetylacetone, a β-diketone, with 2 moles of diethyl phosphite was reported by B. A. Arbuzov et al, *Izv. Akad. Nauk. SSSR,* Ser Khim 12, 2757 (1971) to give 2-oxo-2-ethoxy-3-hydroxy-3,5-dimethyl-5-diethylphosphono-1,2-oxaphospholane. This compound, although somewhat related to the compounds of this invention, possesses quite different chemical properties due to the 3-hydroxy group, and can undergo a variety of chemical reactions unavailable to the instant compounds.

DETAILED DISCLOSURE

This invention pertains to new 1,2-oxaphospholane-5-phosphonic acid esters, a process for their manufacture, a method of using them as flameproofing agents for epoxy resins, and also, epoxy resin products protected by them.

The new compounds have the general formula I

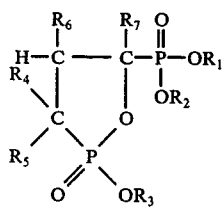

(I)

wherein each of $R_1$, $R_2$ and $R_3$ independently represents a monovalent aliphatic radical, or each of $R_4$, $R_5$ and $R_6$ independently represents hydrogen or alkyl, and $R_7$ represents alkyl.

A monovalent aliphatic radical represented by $R_1$, $R_2$ or $R_3$ can be a linear or branched alkyl of 1 to 18 carbon atoms such as methyl, ethyl, isopropyl, n-butyl, 2-ethylhexyl, isooctyl, n-dodecyl and n-octadecyl.

Preferably $R_1$, $R_2$ and $R_3$ are independently alkyl of 1 to 8 carbon atoms such as methyl, ethyl, isopropyl, n-propyl, n-butyl, n-octyl and isooctyl. Most preferably $R_1$, $R_2$ and $R_3$ are independently alkyl of 1 to 4 carbon atoms.

Compounds where $R_3$ is the same as $R_1$ or $R_2$, and preferably where $R_1$, $R_2$ and $R_3$ are the same and are alkyl of 1 to 18 carbon atoms are of particular interest.

Particularly preferred are compounds of formula I where $R_1$, $R_2$ and $R_3$ are the same and are alkyl of 1 to 8 carbon atoms. Still more preferred are compounds where $R_1$, $R_2$ and $R_3$ are the same and are alkyl of 1 to 4 carbon atoms and especially when $R_1$, $R_2$ and $R_3$ are all ethyl.

$R_4$, $R_5$ and $R_6$ independently are hydrogen or methyl, or when $R_4$ is methyl, $R_5$ together with $R_7$ can denote 2,2-dimethyl-1,3-trimethylene. Preferably $R_4$ and $R_5$ are methyl. and $R_6$ is hydrogen, or $R_4$ is methyl, $R_6$ is hydrogen and $R_5$ together with $R_7$ is 2,2-dimethyl-1,3-trimethylene. Most preferably $R_4$ and $R_5$ are methyl and $R_6$ is hydrogen.

$R_7$ is alkyl of 1 to 8 carbon atoms such as methyl, ethyl, n-butyl or n-octyl. Preferably $R_7$ is methyl or ethyl and most preferably $R_7$ is methyl.

Examples of individual compounds of the formula I are the following 1,2-oxaphospholane derivatives:

2-oxo-2-methoxy-5-methyl-5-dimethylphosphono-1,2-oxaphospholane 2-oxo-2-ethoxy-5-methyl-5-diethylphosphono-1,2-oxaphospholane 2-oxo-2-isopropoxy-5-methyl-5-diisopropylphosphono-1,2-oxaphospholane 2-oxo-2-butoxy-5-methyl-5-dibutylphosphono-1,2-oxaphospholane 2-oxo-2-octoxy-5-methyl-5-dioctylphosphono-1,2-oxaphospholane 2-oxo-2-(2-ethylhexyloxy)-5-methyl-5-bis-(2-ethylhexyl)-phosphono-1,2-oxaphospholane 2-oxo-2-octadecyloxy-5-methyl-5-dioctadecylphosphono-1,2-oxaphospholane 2-oxo-2-methoxy-5-ethyl-5-dimethylphosphono-1,2-oxaphospholane 2-oxo-2-ethoxy-5-ethyl-5-diethylphosphono-1,2-oxaphospholane 2-oxo-2-methoxy-3,5-dimethyl-5-dimethylphosphono-1,2-oxaphospholane 2-oxo-2-ethoxy-3,5-dimethyl-5-diethylphosphono-1,2-oxaphospholane 2-oxo-2-methoxy-3,4-dimethyl-5-dimethylphosphono-1,2-oxaphospholane 2-oxo-2-ethoxy-3,4-dimethyl-5-diethylphosphono-1,2-oxaphospholane 2-oxo-2-methoxy-3,3,5-trimethyl-5-dimethylphosphono-1,2-oxaphospholane 2-oxo-2-ethoxy-3,3,5-trimethyl-5-diethylphosphono-1,2-oxaphospholane 2-oxo-2-isopropoxy-3,3,5-trimethyl-5-diisopropylphosphono-1,2-oxaphospholane 2-oxo-2-butoxy-3,3,5-trimethyl-5-dibutylphosphono-1,2-oxaphospholane 2-oxo-2-(2-ethylhexyloxy)-3,3,5-trimethyl-5-bis-(2-ethylhexyl)-phosphono-1,2-oxaphospholane 2-oxo-2-isopropoxy-3,5-dimethyl-5-dimethylphosphono-1,2-oxaphospholane 1-diethylphosphono-3,3,5-trimethyl-6-oxo-6-ethoxy-7-oxa-6-phosphabicyclo[3.2.1]octane 1-dimethylphosphono-3,3,5-trimethyl-6-oxo-6-methoxy-7-oxa-6-phosphabicyclo[3.2.1]octane The surprising discovery has been made that it is possible to manufacture the compounds of the formula I, in which $R_3$ is the same as $R_1$ or $R_2$, or preferably where $R_1$, $R_2$ and $R_3$ are all the same, by a novel process which comprises reacting one mole of an α, β-unsaturated ketone of the formula II

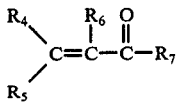
(II)

with at least two moles of a phosphite of the formula III

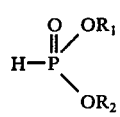
(III)

in the presence of a base, with or without the addition of a solvent.

Examples of commercially available α, β-unsaturated ketones of the formula II are methyl vinyl ketone, ethyl vinyl ketone, mesityl oxide, methyl isopropenyl ketone, isophorone and 3-penten-2-one. Such ketones can be manufactured by known methods, for example by condensation of the appropriate methyl ketones with aldehydes or ketones. For reasons of availability and cost, mesityl oxide is preferred. Other α, β-unsaturated ketones useful in this invention include α-ionone, β-ionone, 4-methoxy-3-buten-2-one and phorone.

The phosphites of the formula III are known compounds of industrial availability. Examples thereof are dialkyl phosphites, such as dimethyl, diethyl or dioctyl phosphite, and mixed phosphites, such as methyl butyl phosphite.

In the reaction there are used 2 moles, preferably 2.0 to 3.5 moles, of a compound of the formula III for each mole of the compound of the formula II.

Although the stoichiometry of the reaction of a phosphite of formula III with an α, β-unsaturated ketone of formula II to form the oxaphospholanes of formula I requires 2 moles of phosphite for each mole of α, β-unsaturated ketone, the nature of the chemistry involved is such that when only equimolar amounts of the phosphite and ketone are employed significant quantities of the corresponding oxaphospholane along with some of the corresponding 1 to 1 adduct, namely a γ-ketophosphonate, as well as some unreacted α, β-unsaturated ketone are formed. In the case of the base catalyzed reaction of equimolar amounts of diethyl phosphite and mesityl oxide exemplified in Example 8, a mixture of 43 mole percent γ-ketophosphonate and 26 mole percent of the oxaphospholane along with unreacted mesityl oxide was obtained accounting for 95 percent of the diethyl phosphite used.

Because of the requirement of separating the desired oxaphospholane from the mixture containing the corresponding γ-ketophosphonate, the reaction of equimolar amounts of a phosphite of formula III with a ketone of formula II is not a preferred process for preparing oxaphospholanes of Formula I. However, it does provide an operable route to the preparation of oxaphospholanes.

Examples of bases which catalyze the reaction are principally alkali metals, alkali metal or alkaline earth metal alkoxides, alkali metal amides and hydrides. Particularly effective are metals, sodium or potassium, sodium ethoxide, sodium methoxide, potassium tert.-butoxide, lithium amide and calcium hydride. Normally, catalytic amounts of these bases suffice to initiate the reaction. It is sometimes advantageous to add further amounts of base during the reaction.

If the process according to the invention is carried out with the addition of a solvent, then suitable solvents are primarily hydrocarbons, e.g., benzene, toluene, xylene, ligroin, hexane or heptane, also alcohols, e.g., methanol, ethanol or isopropanol, or ethers, e.g., diethyl ether, dioxane or tetrahydrofuran. However, a solventless process as illustrated in an appended example is preferred.

The reaction can be carried out by dissolving the ketone of the formula II and adding dropwise a portion of the phosphite of the formula III and the base. Upon onset of the reaction, the remainder of the phosphite and, if necessary, further amounts of base are added by gradual amounts. It is also possible to premix the phosphite with the catalyst and to add the ketone of the formula II dropwise.

In another embodiment, the compounds of the formulas II and III and optionally the solvent are first mixed and then the base, which can also be dissolved in the solvent, is added to this mixture and the reaction is brought to completion by heating.

The oxaphospholanes of the formula I are isolated by customary methods, for example by distillation. Desirably the base is neutralized before the isolation by an equivalent amount of an acid, for example acetic acid.

It has furthermore been found that oxaphospholane derivatives of the formula I can also be manufactured from the known γ-ketophosphonates by addition of dialkyl phosphites. This is an indication that the reaction discussed above probably proceeds via the stage of the γ-ketophosphonates. It is therefore possible to carry out the reaction in two partial steps, the first being the known addition of one mole of phosphite to α, β-unsaturated ketones to form the γ-ketophosphonates and the second being the reaction with a second mole of phosphite to form the oxaphospholanes. This second step is just as surprising and novel as the single step main process.

The invention therefore also provides a process for the manufacture of compounds of the formula I, which comprises reacting one mole of a compound of the formula IV

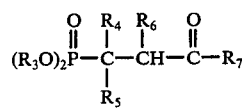
(IV)

with at least one mole of a phosphite of the formula III in the presence of a base, with or without the addition of a solvent. In the formula IV, the substituents $R_3$ to $R_7$ have the same meanings assigned to them as in respect of the compounds of the formula I. The catalysts and solvents suitable for use in this process are the same as those for the single step main process described hereinbefore, and the reaction and isolation of the products are carried out in the same way.

The modification is principally of importance for the manufacture of those compounds of the formula I in which $R_3$ if different from $R_1$ and $R_2$.

The compounds of the formula I are outstanding flameproofing agents for epoxy resins. It has long been known that phosphorus-containing compounds can be used as flameproofing agents for polymers, but it is normally necessary to use the phosphorus compounds in high concentrations, which results as a rule in a deterioration of the physical properties of the polymers.

The surprising discovery has now been made that the new 1,2-oxaphospholanes of the formula I impart an adequate flame resistance to the polymers even in relatively low concentrations. Moreover, they have only a minute influence on the physical properties of the substrates. Further, they are also usable in reactive systems, such as in epoxy resins.

The introduction of flameproofing agents of formula I can be accomplished by adding them to the starting components of an epoxy resin formulation. These resins are usually manufactured by mixing an epoxide component with a hardener component, whereupon a polyaddition reaction takes place between the two components. The flame-proofing agents of the formula I can be mixed both with the epoxide and with the hardener component since they are compatible with both, and such mixtures are storable. But it is also possible to add the flameproofing agent only during the manufacture of the resin as a third component.

Epoxy resins are used frequently in those cases where a high thermal stability of a resin under load is required. Many organic flameproofing agents, for example, phosphorus esters or chloroparaffins, effect a perceptible reduction in the thermomechanical stability of epoxy resins. However, such small amounts of the compounds of the formula I are required for an effective flameproofing of epoxy resins that the thermomechanical stability of these latter is not substantially impaired.

The compounds of the formula I are normally added to the cited substances in an amount of 2 to 30% by weight, preferably 2 to 10% by weight, based on the substrate. The addition can be carried out before or during the manufacture of the substrate by polymerization; but frequently the compounds are added to the finished polymers before or during their processing.

In addition to the flameproofing agents of the formula I, it is also possible to add to the polymeric substrates other flameproofing agents, e.g., organic halogen compounds, antimony oxide or other phosphorus compounds. It is furthermore possible to add other customary and known additives, e.g., antioxidants, heat stabilizers, UV absorbers, fluorescent brighteners, antistatic agents, lubricants, softeners, emulsifiers, pigments, carbon black, asbestos, kaolin, talcum, glass fibers or other fillers and reinforcing agents.

The manufacture and utility of the oxaphospholanes of the formula I are illustrated in more detail in the following Examples.

EXAMPLE 1

2-Oxo-2-ethoxy-3,3,5-trimethyl-5-diethylphosphono-1,2-oxaphospholane 10 ml of diethyl phosphite was added to a solution of 98.1 g (1 mole) of mesityl oxide in 300 ml of benzene, and the mixture was then heated to 80° C. About 200 mg of metallic sodium was added to the almost boiling solution, whereupon an exothermic reaction commenced. The reaction was brought to completion over the course of 10 minutes by gradual addition of altogether 345.0 g (2.5 moles) of diethyl phosphite and 4.2 g of sodium. The reaction mixture was stirred for an additional 10 minutes, neutralized with 11 g of glacial acetic and evaporated in vacuum. The residue was distilled in high vacuum. The main fraction distilled as an almost colorless oil at 136°-139° C and 0.035 mm Hg. Analysis by nuclear magnetic resonance and mass spectrum showed this fraction to be 2-oxo-2-ethoxy-3,3,5-trimethyl-5-diethylphosphono-1,2-oxaphospholane of the empirical formula $C_{12}H_{26}O_6P_2$ (MW = 328.29).

Analysis: Calc: C, 43.90; H, 7.99; P, 18.92.
Found: C, 44.30; H, 8.00, P, 18.0.
The yield was 45.3% of theory.

The same reaction was carried out with 392 g (4 moles) of mesityl oxide and 1,660 g (12 moles) of diethyl phosphite in 1,200 ml of benzene and in the presence of 9.5 g of sodium. Upon completion of the reaction (40 minutes), the reaction mixture was neutralized with 24.8 g of glacial acetic acid and distilled to yield 995.7 g of 2-oxo-2-ethoxy-3,3,5-trimethyl-5-diethylphosphono-1,2-oxaphospholane at 136°-140° C at 0.02-0.04 Torr. This corresponded to a yield of 75.9% of theory.

EXAMPLE 2

2-Oxo-2-methoxy-3,3,5-trimethyl-5-dimethylphosphono-1,2-oxaphospholane

A solution of 30.0 g of sodium methoxide in 90 ml of methanol was added dropwise to a mixture of 220 g of dimethyl phosphite and 98 g of mesityl oxide over the course of 2 hours in such a way that the reaction temperature did not exceed 65° C. The clear solution was subsequently heated for 2 hours to 70° C. The reaction mixture was concentrated in vacuo and the residue was taken up in 200 ml of toluene. The solution was filtered and the filtrate distilled. The 2-oxo-2-methoxy-3,3,5-trimethyl-5-dimethylphosphono-1,2-oxaphospholane distilled at 158° C-160° C at 0.6 mm Hg in the form of a colorless, viscous oil.

Analysis for, $C_9H_{20}O_6P_2$ (MW = 286.20): Calc: C, 37.80; H, 7.05; P, 21.65.
Found: C, 37.79; H, 7.04; P, 21.32.

EXAMPLE 3

2-Oxo-2-ethoxy-3,3,5-trimethyl-5-diethylphosphono-1,2-oxaphospholane

A dry 3,000 ml three-necked flask with mechanical stirrer, thermometer and 800 ml addition funnel was charged with 1,381 g (10.0 moles) of diethyl phosphite and 100 g of a solution containing 0.25 moles of sodium ethoxide in absolute ethanol.

Without an external heating or cooling bath 491 g (about 570 ml, 5.0 moles) of mesityl oxide was then added evenly at a rate of about 15 ml/min. from the addition funnel. The addition reaction was strongly exothermic. The temperature of the reaction mixture rose from 24° C to 95° C during the initial 20 minutes, at which point half of the mesityl oxide had been added. The temperature then dropped gradually to 70° C while the remaining half of mesityl oxide was added, again over a 20-minute period. The resulting clear orange solution was stirred for additional 50 minutes, after which the final temperature was 46° C.

To reinitiate the reaction, an additional 50 g of sodium ethoxide solution was added all at once, causing an immediate temperature to rise to 106° C over a 3-minute period. The temperature then gradually fell to 70° C on further stirring for 30 minutes. Another portion of diethyl phosphite (69 g = 0.5 moles), was added (no exotherm) followed by additional 50 g of sodium ethoxide solution (weak exotherm; 3° C temperature rise).

After continued stirring without heating for 2½ hours, conversion was largely complete. The product obtained consisted of 93% 2-oxo-2-ethoxy-3,3,5-trimethyl-5-diethyl-phosphono-1,2-oxaphospholane and 7% ketophosphonate.

The reaction mixture was neutralized with 30.0 g (0.5 moles) of glacial acetic acid. Volatile components were removed by distillation, finally at 100° C pot temperature and at 20 mm Hg, yielding 1,750 g of an orange oil (94% of the oxaphospholane compound and 6% of the ketophosphonate), in essentially quantitative yield. Subsequent vacuum distillation yielded a forerun containing residual volatiles, the ketophosphate and some oxaphospholane compound (311 g, b.p. to 160° C/0.5 mm) followed by 1,260 g of pure 2-oxo-2-ethoxy-3,3,5-trimethyl-5-diethylphosphono-1,2-oxaphospholane (b.p. 162°–168° C/0.5 mm Hg) yield 76.8% of theory, with a purity of 99.4% as determined by gas phase chromatography.

Analysis for $C_{12}H_{26}O_6P_2$ (MW 328.3): Calc: C, 43.90; H, 7.90; P, 18.87. Found: C, 43.88; H, 7.89; P, 18.56.

The H-NMR Spectrum (100 MHz, $CDCl_3$) was consistent for the structure and no impurities were evident.

1.18–1.80 ppm — 18 H (6 methyl groups)
1.80–2.90 ppm — 2 H (1 ring-methylene group)
4.20 ppm — 6 H (3 ester methylene groups)

EXAMPLE 4

2-Oxo-2-ethoxy-3,3,5-trimethyl-5-diethylphosphono-1,2-oxaphospholane 98 g of mesityl oxide (1.0 mole) and 415 g of diethyl phosphite (3.0 moles) were dissolved in 300 ml of benzene. 200 ml of this solution was heated to the boiling point. A catalytic amount of sodium was added whereupon a vigorous exothermic reaction commenced, and the mixture boiled by itself after removal of the heating bath. After the sodium dissolved, the reaction came practically to a stop and was initiated again by addition of a further amount of sodium. In this manner sodium was added until the main reaction was over. Then about one third of the remaining solution was added, and this was also reacted as previously by adding sodium. The remaining two thirds of the solution were then reacted in the same way. Altogether 3.0 g of sodium was used over the course of 25 minutes. The entire reaction mixture was allowed to continue to react for 15 minutes at reflux. It was then neutralized with 8 g of glacial acetic acid and diluted with 350 ml of benzene. After the reaction solution cooled, it was washed with two portions of water of 75 and 20 ml respectively. The combined aqueous phases were extracted with 50 ml of benzene twice to give a solution in benzene which was combined with the chief portion, dried with $Na_2SO_4$ and concentrated in a rotary evaporator. Distillation yielded 118.5 g of a first fraction of b.p. 46°–68° C/8 mm Hg, which largely consisted of diethyl phosphite, and 280.8 g (85.6% of theory) of the oxaphospholane which boiled at 122°–132° C. at 0.008 mm Hg. Gas chromatography showed the product to be about 95% pure. 8.2 g remained as the distillation residue.

EXAMPLE 5

2-Oxo-2-isopropoxy-3,3,5-trimethyl-5-diisopropylphosphono-1,2-oxaphospholane

As described in Example 4, a mixture of 19.6 g of mesityl oxide (0.20 mole), 99.6 g of diisopropyl phosphite (0.60 mole) and 100 ml of benzene was reacted with 2.1 g of sodium as catalyst over the course of 10 minutes. The reaction was vigorously exothermic. After a subsequent reaction for 15 minutes at the boiling temperature, the reaction mixture was neutralized with 5.5 g of glacial acetic acid and diluted with 150 ml of benzene. After the reaction solution cooled, it was extracted with 20 ml of benzene twice, and the extract was combined with the chief portion, dried over $Na_2SO_4$ and concentrated in a rotary evaporator. The distillation yielded 27.5 g of a first fraction with a boiling point of 68°–75° C/10 mm Hg and consisting of virtually pure diisopropyl phosphite as well as 58.0 g (78.3%) of the oxaphospholane which boiled at 120°/0.02 mm Hg to 125° C/0.05 mm Hg; 5.3 g remained as residue.

Analysis, for $C_{15}H_{32}O_6P_2$ (MW = 370.37): Calc: C, 48.64; H, 8.71; P, 16.73. Found: C, 48.77; H, 8.92; P, 16.37.

The mass spectrum showed the molecular peak at $m/e$ 370.

EXAMPLE 6

2-Oxo-2-ethoxy-4,5-dimethyl-5-diethylphosphono-1,2-oxaphospholane

In analogous manner to Example 4, a mixture of 25 g of freshly distilled methyl isopropenyl ketone (0.30 mole), 124 g of diethyl phosphite (0.90 mole) and 75 ml of benzene was reacted with 2.5 g of sodium over the course of 10 minutes. The reaction was vigorously exothermic. After a subsequent reaction for 10 minutes at the boiling temperature, the reaction mixture was neutralized with glacial acetic acid and diluted with 300 ml of benzene. After the reaction solution cooled, it was extracted with 60 ml of $H_2O$. The aqueous phase was extracted twice with 60 and 30 ml of benzene respectively, and the extract was combined with the chief portion, dried over $Na_2SO_4$ and concentrated in a rotary evaporator. Distillation yielded 49.2 g (52.2% of theory) of the oxaphospholane of b.p 128°–132° C/0.002 mm Hg.

Analysis, for $C_{11}H_{24}O_6P_2$ (MW = 314.26). Calc: C, 42.04; H, 7.70; P, 19.71. Found: C, 41.78; H, 7.69; P, 19.39.

The mass spectrum showed the molecular peak at $m/e$ 314.

EXAMPLE 7

2-Oxo-2-butoxy-3,3,5-trimethyl-5-dibutylphosphono-1,2-oxaphospholane

A reaction solution was prepared from 194 g (1 mole) of freshly distilled dibutyl phosphite and 32.4 g (0.33 mole) of mesityl oxide in 200 ml of absolute benzene. 30 ml of this mixture was put into the reaction flask and treated with about 50 mg of sodium. An exothermic reaction commenced and the temperature rose to 70° C. After the reaction subsided, the mixture was brought to reflux temperature by addition of the reaction solution in small amounts of 1.5 g sodium. Stirring was continued for 1 hour at 70° C and the reaction mixture was subsequently neutralized with glacial acetic acid. Distillation yielded the product with a boiling point of 158° C–162° C/0.01 mm.

EXAMPLE 8

2-Oxo-2-ethoxy-3,3,5-trimethyl-5-diethylphosphono-1,2-oxaphospholane

To a stirred mixture of 736 g (7.5 moles) of mesityl oxide and 1036 g (7.5 moles) of diethyl phosphite was added a solution prepared from 2.87 g (0.125 gram-atoms) of sodium in 45 ml of absolute ethanol over a period of 2 hours during which time the temperature rose temporarily to 86° C. The reaction mixture was heated for an additional 2 hours at 88° C. After neutralizing the basic catalyst by addition of 8.4 g of glacial acetic acid, the reaction mixture was fractionally distilled to yield 759 g of diethyl 1,1-dimethyl-3-oxobutyl-phosphonate (43% of theory based on diethyl phosphite), boiling point 143°–146° C at 15 mm Hg, and 639 g of 2-oxo-2-ethoxy-3,3,5-trimethyl-5-diethylphosphono-1,2-oxaphospholane (52% of theory based on diethyl phosphite), a boiling point 165° C at 0.5 mm Hg.

EXAMPLE 9

2-Oxo-2-ethoxy-3,3,5-trimethyl-5-diethylphosphono-1,2-oxaphospholane 690 g of diethyl phosphite and 50 g of a sodium ethoxide solution (17 g of sodium dissolved in 83 g of ethanol) were mixed and with stirring, 245.5 g of mesityl oxide was dropped into this solution over the course of 40 minutes. During the dropwise addition an exothermic reaction took place, the reaction temperature rising from 20° C to 101° C when up to half the amount of mesityl oxide was addd. The temperature then fell to 75° C when the second half of the mesityl oxide was added. The colorless, clear solution was stirred for 50 minutes and the temperature in the reaction mixture fell to 39° C. Then an additional 25 g of sodium ethoxide solution was added all at once, whereupon the temperature of the reaction mixture rose from 39° to 84° C. The reaction mixture was stirred for 30 minutes and then 25 g of sodium ethoxide solution was added. The resultant mixture was stirred for 3 hours at room temperature and subsequently neutralized with 15 g of glacial acetic acid. Distillation of this reaction mixture yielded at 162°–167° C/0.5 mm 626 g of 2-oxo-2-ethoxy-3,3,5-trimethyl-5-diethylphosphono-1,2-oxaphospholane as a colorless liquid. Chromatographic analysis showed at purity of 99.1%.

EXAMPLE 10

2-Oxo-2-ethoxy-5-methyl-5-diethylphosphono-1,2-oxaphospholane 276 g (2 moles) of freshly distilled diethyl phosphite was treated with a solution of 3.5 g of sodium methoxide in 20 ml of absolute ethanol, and 70 g (1 mole) of freshly distilled methyl vinyl ketone was then added dropwise thereto. The exothermic reaction caused the temperature of the mixture to rise to about 70° C. After the whole amount of methyl vinyl ketone was dropped in, stirring was continued for 2 ½ hours and the reaction mixture was neutralized with glacial acetic acid. After a first fraction which consisted largely of diethyl phosphite and methyl vinyl ketone, the distillation at 0.01 mm yielded the product with a boiling point of 120°–133° C.

EXAMPLE 11

2-Oxo-2-ethoxy-5-ethyl-5-diethylphosphono-1,2-oxaphospholane 138 g (1 mole) of freshly distilled diethyl phosphite was treated with a solution of 1.75 g (0.075 mole) of sodium in 10 ml of absolute ethanol, and 42 g (0.5 mole) of ethyl vinyl ketone was then added dropwise thereto. The exothermic reaction caused the temperature of the mixture to rise to 70° C. After the whole amount of ethyl vinyl ketone was dropped in, the reaction was brought to completion by adding another 1 g (0.04 mole) of sodium in 10 ml of absolute alcohol with a rise in temperature to 60° C observed. Stirring was continued for 2 hours and the reaction mixture was then neutralized with glacial acetic acid. After a first fraction which consisted largely of diethyl phosphite and ethyl vinyl ketone, the distillation of 0.1 mm yielded the product having a boiling point of 132°–138° C.

EXAMPLE 12

2-Oxo-2-ethoxy-3,3,5-trimethyl-5-diethylphosphono-1,2-oxaphospholane

To a mixture of 2.36 grams (10 m moles) of 4-methyl-4-diethylphosphonopentan-2-one (prepared from 1 mole of mesityl oxide and 1 mole of diethyl phosphite by the procedure of A. N. Pudovik, *Zhurn Obshch. Khim.*, 22, 1371 (1952) and 1.64 grams (11.9 m moles) of diethyl phosphite was added 0.30 grams of ethanolic sodium ethoxide solution containing 0.75 m moles of sodium ethoxide. A spontaneous exothermic reaction took place immediately. After 5 minutes the reaction mixture was analyzed by gas phase chromatography and was shown to contain over 70% of the desired 2-oxo-2-ethoxy-3,3,5-trimethyl-5-diethylphosphono-1,2-oxaphospholane. The product was then isolated by vacuum distillation as described in Example 3.

EXAMPLE 13

2-Oxo-2-ethoxy-3,3,5-trimethyl-5-diethylphosphono-1,2-oxaphospholane 10 ml of a mixture of 70.8 g of 4 methyl-4-(diethylphosphono)-pentan-2-one (prepared from mesityl oxide and diethyl phosphite) and 82.8 g of diethyl phosphite were dissolved in 100 ml of toluene, and the solution was heated to 80° C. A catalytic amount of sodium was added and a vigorous exothermic reaction commenced. The reaction temperature was held between 80° C and 90° C by alternatively adding the previously prepared mixture and small pieces of sodium. Altogether 1.65 g of sodium was used as catalyst. The reaction took 20 minutes. The reaction mixture was subsequently stirred at 80°-90° C for 30 minutes with heating, then cooled and neutralized with 4.5 g of glacial acetic acid. This reaction mixture was distilled to yield 2-oxo-2-ethoxy-3,3,5-trimethyl-5-diethylphosphono-1,2-oxaphospholane with a boiling point of 156°–161° C/1.1 mm. This substance is identical to the oxaphospholane manufactured according to Example 4.

EXAMPLE 14

2-Oxo-2-ethoxy-3,3,5-trimethyl-5-dimethylphosphono-1,2-oxaphospholane

By carrying out the same procedure as described in Example 13, 2-oxo-2-ethoxy-3,3,5-trimethyl-5-dimethylphosphono-1,2-oxaphospholane with a boiling point of 146°–148° C/0.5 mm was obtained from 70.8 g of 4-methyl-4-(diethylphosphono)-pentan-2-one and 66.0 g of dimethyl phosphite with 1.65 g of sodium as catalyst.

EXAMPLE 15

2-Oxo-2-ethoxy-3,3,5-trimethyl-5-diisopropylphosphono-1,2-oxaphospholane

By carrying out the same procedure as described in Example 13, 2-oxo-2-ethoxy-3,3,5-trimethyl-5-diisopropylphosphono-1,2-oxaphospholane with a boiling point of 180°–185° C/2 mm was obtained from 70.8 g of 4-methyl-4-(diethylphosphono)-pentan-2-one and 99.6 g of diisopropyl phosphite with 4.6 g of sodium as catalyst.

EXAMPLE 16

2-Oxo-2-methoxy-3,3,5-trimethyl-5-diethylphosphono-1,2-oxapospholane

By carrying out the same procedure as described in Example 13, 2-oxo-2-methoxy-3,3,5-trimethyl-5-diethylphosphono-1,2-oxaphospholane with a boiling point of 144°–146° C/0.6 mm was obtained from 83.2 g of 4-methyl-4-(dimethylphosphono)-pentan-2-one and 110.4 g of diethyl phosphite with 1.15 g of sodium as catalyst. The $P^{31}$ spectrum showed for the phosphorus atom in the ring a shift of −48 ppm compared with $H_3PO_4$ as standard.

EXAMPLE 17

2-Oxo-2-ethoxy-3,3,5-trimethyl-5-diisooctylphosphono-1,2-oxaphospholane

By carrying out the same procedure as described in Example 13, 2-oxo-2-ethoxy-3,3,5-trimethyl-5-diisooctylphosphono-1,2-oxaphospholane was obtained as a viscous, colorless oil from 47.2 g of 4-methyl-4-(diethylphosphono)-pentan-2-one and 84.6 g of diisooctyl phosphate with 1.15 g of sodium as catalyst. The $P^{31}$ spectrum of this oil showed for the phosphorus atom in the ring a shift of −49 ppm compared with $H_3PO_4$ as standard.

EXAMPLE 18

2-Oxo-2-ethoxy-3,3,5-trimethyl-5-di-n-octylphosphono-1,2-oxaphospholane

By carrying out the same procedure as described in Example 13, 2-oxo-2-ethoxy-3,3,5-trimethyl-5-di-n-octylphosphono-1,2-oxaphospholane was obtained as a viscous, pale yellow oil from 47.2 of 4-methyl-4-(diethylphosphono)-pentan-2-one and 84.6 g of di-n-octyl phosphite with 1.15 g of sodium as catalyst. The $p^{31}$ spectrum of this oil showed for the phosphorous atom in the ring a shift of −49 ppm compared with $H_3PO_4$.

EXAMPLE 19

2-Oxo-2-ethoxy-3,3,5-trimethyl-5-di-n-butylphosphono-1,2-oxaphospholane

By carrying out the same procedure as described in Example 13, 2-oxo-2-ethoxy-3,3,5-trimethyl-5-di-n-butylphosphono-1,2-oxaphospholane is obtained from reacting 4-methyl-4-(diethylphosphono)-pentan-2-one and di-n-butyl phosphite.

EXAMPLE 20

2-Oxo-2-propyloxy-3,3,5-trimethyl-5-dipropylphosphono-1,2-oxaphospholane 11.8 g of mesityl oxide and 9.8 g of dipropyl phosphite were heated in 40 ml of benzene to 80° C. At this temperature, 0.1 g of sodium was added, whereupon an exothermic reaction commenced. The reaction temperature was held at 80°–90° C without external heating by alternately adding 40.0 g of dipropyl phosphite and 0.4 g of sodium. After all the sodium was added, stirring was continued for 30 minutes. The reaction mixture was then cooled and neutralized with 1.4 g of glacial acetic acid. The reaction mixture was concentrated in a rotary evaporator and then distilled in a high vacuum to yield 2-oxo-2-ethoxy-3,3,5-trimethyl-5-dipropylphosphono-1,2-oxophospholane in the form of a colorless oil with a boiling point of 153°–154° C/0.1 mm. The $P^{31}$ spectrum showed for the phosphorus atom in the ring a shift of −67.2 ppm compared with triphenyl phosphate as standard.

EXAMPLE 21

1-Diethylphosphono-3,3,5-trimethyl-6-oxo-6-ethoxy-7-oxa-6-phosphabicyclo[3.2.1]octane When in Example 3 an equivalent amount of isophorone was substituted for the mesityl oxide, the above-identified product was obtained.

EXAMPLE 22

Flameproofing of epoxy resins

A rigid form based on epoxide resin was manufactured from the following constituents:
resin:
 105 parts of epoxide resin based on bisphenol A with an epoxide equivalent weight of 190
 45 parts of epoxide resin based on bisphenol A with an epoxide equivalent weight of 400
 2 parts of foam stabilizer Si 3193 (Messrs. Rhodia; a glycol-silicone copolymer)
 5 parts of pentane
 5 parts of trichloromonofluoromethane
hardener:
 7 parts of diethylenetriamine
 7 parts of di-(aminomethyl)-cyclohexylmethane
 1 part of bisphenol A
 12 parts of 1,6-diamino-2,4,4-trimethylhexane 3 parts of phenol Resin and hardener are throughly mixed at room temperature and poured into a wooden mold. The foam is removed after 1 hour; it has a density of 0.1g/cm².

Specimen rods measuring 10 × 15 × 120 mm are cut from the rigid foam and subjected to flammability test according to ASTM 635. In this test the rod is hung at an angle of 45° and ignited at its bottom end with a gas flame. The combustion time up to the 10 cm mark is measured and the combustion speed is calculated therefrom. The rigid epoxide foam has a combustion speed of 2 sec./cm.

An epoxide foam of the same composition is manufactured except that 25 parts of 2-oxo-2-ethoxy-3,3,5-trimethyl-5-diethylphosphono-1,2-oxaphospholane are additionally mixed with the resin. The test of this foam by ASTM 635 shows that the resin is self-extinguishing: the measurement mark is not reached.

EXAMPLES 23 to 24

Flameproofing of Epoxy Resins

Several epoxy resin formulations were prepared, two without and four with the oxaphospholane of Example 3 present. The physical properties and flammability data on cured resin specimens prepared from said formulations are given on Table I. The effectiveness of the 1,2-oxaphospholane in conferring good flame retardancy while maintaining very acceptable physical properties is clearly demonstrated.

mixture, was compared to a phosphorus-free formulation of the same resin, as well as to a typical commercial flame retardant epoxy resin formulation that contained 15% bromine. The data are summarized in the following Table II.

TABLE I

|  | Example 23 | Example 24 | Example 25 | Example 26 | Example 27 | Example 28 |
|---|---|---|---|---|---|---|
| **Formulations* (parts by weight)** | | | | | | |
| Oxaphospholane | — | — | 17.8 | 17.7 | 28.3 | 28.3 |
| Epoxy Resin ARALDITE 6010 | 55.2 | 88.5 | 69.7 | 41.5 | 60.6 | 63.5 |
| Hexahydrophthalic Anhydride | — | — | — | 40.2 | — | — |
| Liquid Anhydride Hardener | 44.2 | — | — | — | — | — |
| Triethylenetetramine | — | 11.5 | 12.5 | — | 11.1 | 8.2 |
| Benzyldimethylamine | 0.6 | — | — | 0.6 | — | — |
| Phosphorus Content of Formulation | None | None | 3.3% | 3.3% | 5% | 5% |
| Cure | | | | | | |
| Processing | 100° C/15 min | 25° C/75 min | 27° C/60 min | 40° C/25 min | 25° C/60 min | 25° C/60 min |
| Gelling | 100° C/17 hrs | 55° C/17 hrs | 55° C/16 hrs | 90° C/16 hrs | 55° C/17 hrs | 55° C/17 hrs |
| Postcure | 150° C/2 hrs | 100° C/2 hrs | 100° C/2 hrs | 150° C/2 hrs | 100° C/2 hrs | 100° C/2 hrs |
| Physical Properties (at 25° C) | | | | | | |
| Flexural Strength (Kpsi) | 15.5 | >14.6 | >14.9 | >17.0 | >14.1 | >14.0 |
| Flexural Modulus (Kpsi) | 430 | 404 | 428 | 459 | 460 | 466 |
| Tensile Strength (Kpsi) | — | 10.2 | 8.8 | 7.9 | 6.6 | 8.0 |
| Tensile Modulus (Kpsi) | — | 352 | 415 | 367 | 362 | 425 |
| Elongation Yield % (at 25° C) | — | — | 5.5% | 4.0% | 3.7% | — |
| Break (%) (at 25° C) | — | 6.8% | 8.8% | 5.7% | 7.4% | 2.6% |
| Flammability Characteristics | | | | | | |
| Limiting Oxygen Index | 19.4 | 22.0 | 25.6 | 25.0 | 26.6 | 27.6 |
| Flame Spread | UL100 | UL100 | UL$_{100}^a$ | UL$_{100}^{25}$ | UL$_0^a$ | UL$_0^a$ |

*Formulations
Oxaphospholane is 2-oxo-2-ethoxy-3,3,5-trimethyl-5-diethylphosphono-1,2-oxaphospholane (Example 3)
Epoxy Resin A is ARALDITE 6010, comercially available from CIBA-GEIGY Corporation.
Liquid Anhydride hardener is ARALDITE 917, comercially available from CIBA-GEIGY Corporation.
Test procedures are:
Flexural Strength according to ASTM D790
Flexural Modulus according to ASTM D790
Tensile Strength according to ASTM D638
Tensile Modulus according to ASTM D638
Elongation according to ASTM D638
Limiting Oxygen Index according to ASTM D2863-FO. General Electric Flammability Gauge was used for all tests.
Flame Spread according to Underwriter's Laboratories, Inc. "UL94" (tests for flammability of plastic materials).
"UL94" vertical burning test was used for all cases unless marked otherwise. 94VE ratings are used where applicable. UL$_a^b$ ratings are an indication of the time the sample burned where:
  a = average time (in seconds) to self-extinguish after first lighting (rounded to the nearest 5 seconds)
  b = average time (in seconds) to self-extinguish after second lighting (rounded to nearest 5 seconds)

Table II

|  | Example 29 Formulation with 5% P | Example 30 Blank | Example 31 Formulation with 15% Br. |
|---|---|---|---|
| **Formulations* (parts by weight)** | | | |
| Oxaphospholane | 27.0 | — | — |
| Epoxy resin A | — | — | 32.6 |
| Epoxy resin B | 37.6 | 55.0 | — |
| Brominated Epoxy resin | — | — | 30.1 |
| Hexahydrophthalic anhydride | 34.8 | 45.0 | — |
| Liquid anhydride hardener | — | — | 37.4 |
| Limiting Oxygen Index | 29.2 | 19.6 | 27.2 |
| Flame Spread | UL$_0^0$ | Burned Completely | UL$_0^5$ |
| Vertical Flame Test "UL94" | 94VE-0 | Burned Completely | 94VE-1 |

*Formulations
Oxaphospholane is 2-oxo-2-ethoxy-3,3,5-trimethyl-5-diethylphosphono-1,2-oxaphospholane (Example 3)
Epoxy Resin A is ARALDITE 6010, commercially available from CIBA-GEIGY Corporation.
Epoxy Resin B is ARACAST XB2818, commercially available from CIBA-GEIGY Corporation.
Brominated Epoxy Resin is ARALDITE LT8049, commercially available from CIBA-GEIGY Corporation.
Liquid Anhydride hardener is ARALDITE 917, commercially available from CIBA-GEIGY Corporation.
The Limiting Oxygen Index indicates the minimum oxygen content in a nitrogen-oxygen mixture at which the test specimen just still continues to burn.
Limiting Oxygen Index according to ASTM D2863-FO. General Electric Flammability Gauge was used for all tests.
Flame Spread according to Underwriter's Laboratories, Inc. "UL94" (tests for flammability of plastic materials).
"UL94" vertical burning test was used for all cases unless marked otherwise. 94VE ratings are used where applicable. UL$_a^b$ ratings are an indication of the time the sample burned where:
  a = average time (in seconds) to self-extinguish after first lighting (rounded to the nearest 5 seconds)
  b = average time (in seconds) to self-extinguish after second lighting (rounded to nearest 5 seconds)

EXAMPLES 29 to 31

The flammability and smoke density characteristic of an epoxy resin formulation containing 27% of an oxaphospholane, equivalent to 5% phosphorus in the resin

What is claimed is:
1. A compound of the formula

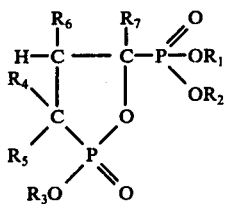

wherein each of $R_1$, $R_2$ and $R_3$ independently denotes alkyl of 1 to 18 carbon atoms; each of $R_4$, $R_5$ and $R_6$ independently denotes hydrogen or methyl; and $R_7$ denotes alkyl of 1 to 8 carbon atoms or when $R_4$ is methyl, $R_6$ is hydrogen, $R_5$ together with $R_7$ can denote 2,2-dimethyl-1,3-trimethylene.

2. A compound according to claim 1 wherein each of $R_1$, $R_2$ and $R_3$ independently denotes alkyl of 1 to 8 carbon atoms; $R_4$ and $R_5$ are methyl; $R_6$ is hydrogen; and $R_7$ is methyl or ethyl, or when $R_4$ is methyl, $R_5$ together with $R_7$ can be 2,2-dimethyl-1,3-trimethylene.

3. A compound according to claim 1 wherein each of $R_1$, $R_2$ and $R_3$ independently denotes alkyl of 1 to 8 carbon atoms; $R_4$ and $R_5$ are methyl; $R_6$ are hydrogen; and $R_7$ is methyl.

4. A compound according to claim 3 wherein each of $R_1$, $R_2$ and $R_3$ independently denotes alkyl of 1 to 4 carbon atoms.

5. A compound according to claim 1 wherein $R_3$ is the same as $R_1$ or $R_2$, and $R_1$, $R_2$ and $R_3$ are alkyl of 1 to 18 carbon atoms.

6. A compound according to claim 1 wherein $R_1$, $R_2$ and $R_3$ are the same and are alkyl of 1 to 8 carbon atoms.

7. A compound according to claim 6 wherein $R_1$, $R_2$ and $R_3$ are the same and are alkyl of 1 to 4 carbon atoms.

8. The compound of claim 7 which is 2-oxo-2-ethoxy-3,3,5-trimethyl-5-diethylphosphono-1,2-oxaphospholane.

9. The compound of claim 7 which is 2-oxo-2-methoxy-3,3,5-trimethyl-5-dimethylphosphono-1,2-oxaphospholane.

10. The compound of claim 7 which is 2-oxo-2-isopropoxy-3,3,5-trimethyl-5-diisopropylphosphono-1,2-oxaphospholane.

11. The compound of claim 7 which is 1-diethylphosphono-b 3,3,5-trimethyl-6-oxo-6-ethoxy-7-oxa-6-phosphabicyclo[3.2.1]-octane.

* * * * *